United States Patent [19]

Capetola et al.

[11] 4,315,936
[45] Feb. 16, 1982

[54] ANALGESIC COMPOSITION

[75] Inventors: Robert J. Capetola, Doylestown, Pa.; John L. McGuire, Whitehouse Station, N.J.

[73] Assignee: Ortho Pharmaceutical Corporation, Raritan, N.J.

[21] Appl. No.: 104,495

[22] Filed: Dec. 17, 1979

[51] Int. Cl.$^3$ .................... A61U 31/38; A61U 31/48
[52] U.S. Cl. ................................. 424/260; 424/275
[58] Field of Search .............................. 424/275, 260

[56] References Cited

PUBLICATIONS

Chem. Abst. 84-389391x (1976).
Merck Index, 9th (1976), pp. 316, 814, 1194.

Primary Examiner—Stanley J. Friedman
Attorney, Agent, or Firm—Benjamin F. Lambert

[57] ABSTRACT

An analgesic composition comprising a mixture of a centrally-acting analgesic compound and α-methyl-4-[2-thienylcarbonyl] benzene acetic acid is described. Enhancement of the analgesic effect is observed in the combination.

6 Claims, 1 Drawing Figure

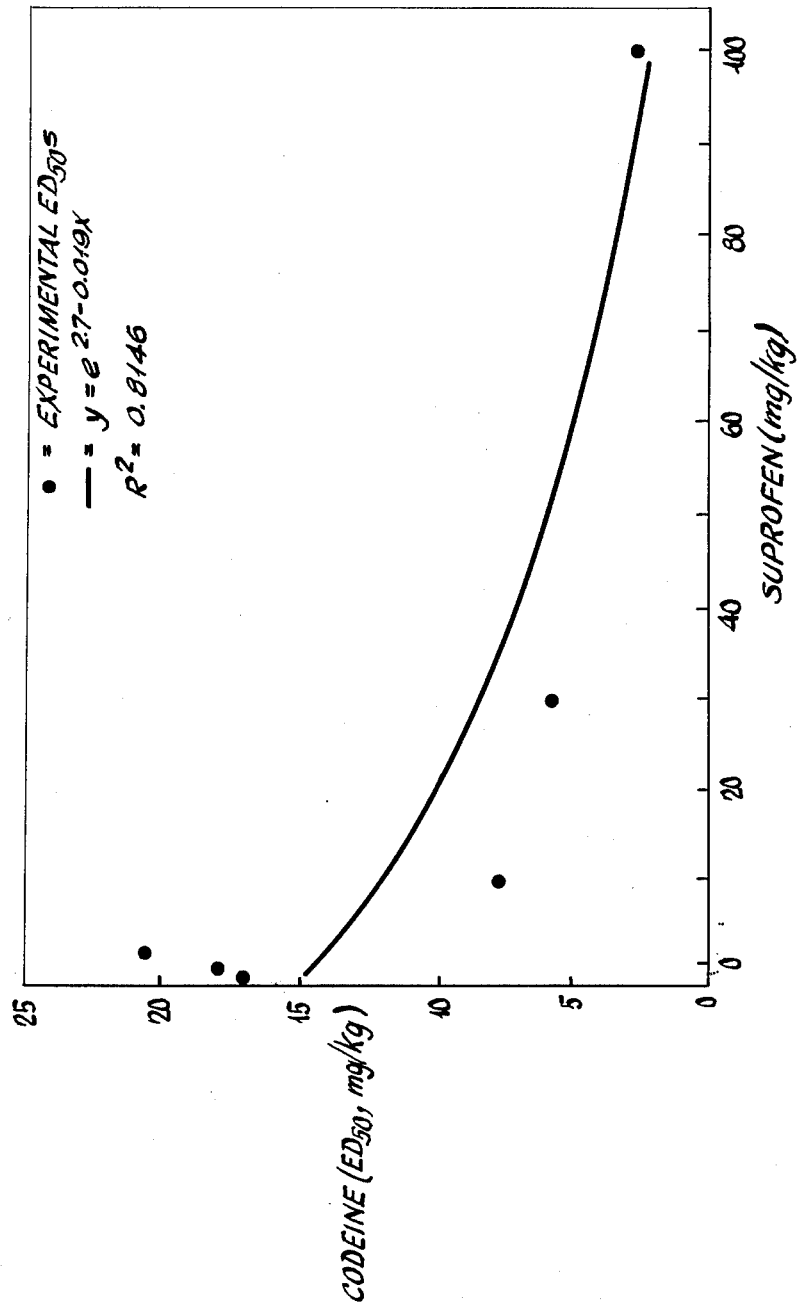

ANALGESIC COMPOSITION

This invention relates to a method of enhancing the potency of certain centrally-acting (narcotic) analgesics by the addition of a non-narcotic (peripheral) analgesic, α-methyl-4-[2-thienylcarbonyl] benzene acetic acid (Suprofen).

The most commonly employed method of managing pain involves the systemic administration of analgesics. Analgesics by definition include drugs which through their action on the nervous system reduce or abolish suffering from pain without producing unconsciousness. This result may be brought about in several ways: (1) by interfering with conduction of noxious impulses or abnormal motor responses by direct action on the peripheral nerves or the brain; (2) by changing the attitude or mood of the patient toward pain, by promoting freedom from anxiety, mild euphoria, or a feeling of well-being or by inducing apathy to the painful experience; (3) by producing sedative and soporific effects; (4) by affecting peripheral modulators of pain; and (5) by producing a combination of two or more of these effects.

Close analysis reveals that analgesics comprise several heterogeneous groups of drugs which act on various parts of the physiopsychologic system concerned with pain. These include those which have their effect primarily on the central nervous system, for example, the opiates and those which exert a local action on the pain conduction system, such as salicylates, for example. The analgesics to which the present invention relates are those which affect primarily the central nervous system.

The drugs which comprise the group known as the centrally-acting analgesics include among others the phenanthrene alkaloids of opium such as morphine, codeine and thebaine and the benzylisoquinoline derivatives such as papaverine and noscapine. Other agents with structures and function related to morphine include, hydromorphone, metopon, oxymorphone, levorphanol, hydrocodone, oxycodone and dihydrocodeine. Also included are the etorphine derivatives, phenazocine, methadone, dextromoramide, dipipanone, phenadoxone, meperidine, alphaprodine, anileridine and piminodone. Examples of a synthetic opioid related to the phenylpiperidines include fentanyl. Also included are mixed agonists/antagonists such as butorphanol, cyclazocine and pentazocine.

It may be generally stated that one should always seek and use the minimal effective dose of any drug. This requires the exercise of good clinical judgment, particularly when dealing with pain which is the most subjective of all symptoms.

In selecting the type of analgesic to be employed, the quality and intensity of pain are the most important considerations. Mild pain can be adequately controlled with non-additive analgesics. Opiates and opioids should be postponed until the weaker drugs prove ineffective. It is often desirous to administer a combination of drugs which produces the same result by entirely different mechanisms.

The centrally-acting analgesics may cause a variety of side effects including sedation, constipation, hypotension, nausea, vomiting, increase in cerebrospinal fluid pressure, respiratory depression, physical dependence and tolerance.

There is a serious need, therefore, to develop a combination of drugs that maintains the activity of centrally-acting analgesics, but accomplishes this result by the administration of smaller doses of the centrally-acting drug. One way of achieving this result is to enhance the analgesic activity of a known centrally-acting drug by the addition of a second compound. By enhancing the analgesic effect it is possible to use smaller amounts of each drug in combination and thereby reduce the side effects attendant to a given drug.

One of the objects of the present invention is to provide a method of enhancing the analgesic effect of compounds having known analgesic activity.

Another object of this invention is to provide an analgesic composition comprising one or more known analgesics in combination with a compound which enhances the analgesic effect of the other.

Another object of this invention is to provide a method of controlling pain by the administration of a composition comprising one or more analgesics and a compound which enhances the analgesic activity.

These and other objects of the invention will become apparent from the following detailed description.

α-Methyl-4-[2-thienylcarbonyl] benzene acetic acid is a new, orally effective, non-narcotic analgesic which has been shown to be more potent than D-propoxyphene and aspirin. It has been found, however, that the addition of suprofen to certain centrally-acting analgesics, such as, for example, codeine, morphine, thebaine and the like enhances the analgesic activity. Since both compounds are analgesics one would expect the effectiveness of a combination of the two compounds to be merely additive. However, tests have shown that the effectiveness of the combination is not merely the sum of the activity of the components, but rather a new analgesic composition which is more effective in controlling pain than would be expected from the cumulative effect of a combination of the two active ingredients but with none of the undesirable side effects.

The compositions of the present invention consist of a combination of suprofen and a centrally-acting analgesic in an intimate admixture with a pharmaceutically acceptable carrier prepared according to conventional pharmaceutical techniques. One or more centrally-acting analgesics may be combined with suprofen in forming the composition. The carrier may take a wide variety of forms depending upon the form of preparation desired for administration, i.e. oral or parenteral. In preparing the compositions in oral dosage form any of the usual pharmaceutical media may be employed such as, for example, water, glycols, oils, alcohols, flavoring agents, preservative coloring agents and the like in the case of oral liquid preparations such as, for example, suspensions, elixirs and solutions. Carriers such as starches, sugars, diluents, granulating agents, lubricants, binders, disintegrating agents and the like may be employed in the case of solid oral preparations such as, for example, powders, capsules and tablets. Because of their ease in administration, tablets and capsules represent the most advantageous oral dosage unit form. If desired, the tablets may be sugar coated or enteric coated by standard techniques. For parenterals, the carrier will usually comprise sterile water, although other ingredients may be added to aid solubility or for preservative purposes. Injectable suspensions may also be prepared, in which case appropriate liquid carriers, suspending agents and the like may be employed.

The compositions of the present invention will generally contain in addition to the analgesic per dosage unit, i.e. tablet, capsule, powder etc., from about 10 to 600 mg. of suprofen, and preferably from about 50 to 400 mg. The other analgesic ingredient (or ingredients) is generally present in doses ranging from about 5 mg. to about 80 mg. and preferably from about 10 to 65 mg.

The analgesic activity of suprofen and in combination with one or more centrally-acting analgesics is determined by means of the rat adjuvant arthritic flexion test. The model employed is unique in that it represents pathologically induced pain. Experiments are designed to assess the interaction activity of the combination. In a randomized, blind study, ED50 values of the centrally-acting analgesic alone and in combination with five doses of suprofen are plotted. Enhancement is indicated by the exponential decrease in the ED50 values of the centrally-acting agent as a function of suprofen dose.

Methods

The method is described with a combination of suprofen and codeine, however, it may be employed to show the effect of a combination of suprofen and other centrally-acting analgesics.

Polyarthritis is induced in male Lewis strain rats (150–175 g, Charles River) in the injection (0.1 ml) of an antoclaved suspension of Mycobacterium butyricum (0.75 mg) in light mineral oil (blandol) into the distal one-third of the tail. This is designated as day 0. On day 17, the rats are tested for their tendency to vocalize following gentle flexion of the tarso-tibial joint. The rat must vocalize five successive times following five flexions of the joint to be accepted into the test groups.

The following day the drug or drug combinations are administered orally and the number of vocalizations recorded after five flexions at 1 and 2 hours post-drug administration. The data presented in this report include only the 2 hour data, as this is the time of peak activity with suprofen (PRR 1114). Suprofen is solubilized by the stoichiometric addition of 1 N NaOH at the final pH of 6.95. The appropriate concentration is diluted in 2.5 ml of water. Codeine phosphate is freely soluble in water and again the doses are made up to 2.5 ml. The various combinations of suprofen and codeine are admixed to yield a final dosing volume of 5 mg/kg. It should be noted that the following solutions become cloudy when admixed:

| | |
|---|---|
| Codeine 30 mg/kg + Suprofen | 3 mg/kg |
| Codeine 30 mg/kg + Suprofen | 10 mg/kg |
| Codeine 30 mg/kg + Suprofen | 30 mg/kg |
| Codeine 30 mg/kg + Suprofen | 100 mg/kg |

A total of thirty groups (8 rats/group) is used for the entire experiment. Each animal is randomly assigned a cage coded with a particular dose of compound(s) or vehicle and the experiment conducted in a blind manner. The study is designed so that each dose-response curve for codeine (1, 3, 10 and 30 mg/kg) is repeated in the presence of various concentrations of suprofen (1, 3, 10 and 100 mg/kg). For each dose-response curve of codeine (alone or in the presence of a fixed concentration of suprofen), a least square regression of the response is fitted (log 10). The $ED_{50}$ is defined here as that dose required to decrease the number of vocalizations one-half relative to control values.

RESULTS AND DISCUSSION

The analgesic activity of the combination of codeine and suprofen is evaluated in 192 polyarthritic rats using inhibition of the squeak (vocalization) response as the index of activity. Table 1 lists the $ED_{50}$ values for codeine alone and in the presence of various fixed doses of suprofen.

TABLE 1

$ED_{50}$ Values for Codeine or a Combination of Codeine and Suprofen

| Drug or Drug Combination | # Animals | $ED_{50}$ (95% F.L.) |
|---|---|---|
| Suprofen | 32 | 835* |
| Codeine | 32 | 17.09 (8.37, 84.16) |
| Codeine + Suprofen 1.0 mg/kg | 32 | 18.01 (6.90, 757.08) |
| Codeine + Suprofen 3.0 mg/kg | 32 | 20.57 |
| Codeine + Suprofen 10.0 mg/kg | 32 | 7.60 (2.29, 66.92) |
| Codeine + Suprofen 30.0 mg/kg | 32 | 5.65 (2.44, 13.48) |
| Codeine + 100 mg/kg | 32 | 2.59 (0.31, 6.19) |

*The shallow dose response curve generated in this test with suprofen precluded a reasonable estimate of the $ED_{50}$.

FIG. 1 shows the regression of the codeine $ED_{50}$ values with increasing doses of suprofen. No significant antagonism of the analgesic potency occurs with any of the suprofen doses. In contrast, with increasing doses of suprofen, there is an exponential decay ($y = e^{2.7 - 0.019X}$) of the codeine $ED_{50}$ values. The coefficient of correlation of this hyperbola to the experimental $ED_{50}$ values is 0.9026 ($p < 0.05$). The coefficient of correlation using a linear model is $R = 0.7733$. Obviously, the exponential decay model is a better representation of the experimental data. This can be interpreted to mean that with increasing doses of suprofen there is a greater decrease in the amount of codeine required to cause analgesia than would be expected from straight additivity.

What is claimed is:

1. A method of controlling pain in mammals which comprises administering to a mammal an effective amount of a composition comprising from about 10 to 600 mg. of α-methyl-4-[2-thienylcarbonyl] benzene acetic acid and from about 5 to 80 mg. of a centrally-acting analgesic selected from the group consisting of codeine and butorphanol.

2. The method of claim 1 wherein the centrally-active analgesic is codeine.

3. A composition useful in controlling pain in mammals comprising in combination from about 5 to 80 mg. of a centrally-acting analgesic selected from the group consisting of codeine and butorphanol from about 10 to 600 mg of α-methyl-4-[2-thienylcarbonyl] benzene acetic acid and a pharmaceutically acceptable carrier.

4. The composition of claim 3 wherein the centrally-acting analgesic is codeine.

5. The method of claim 1 wherein the centrally-acting analgesic is butorphanol.

6. The composition of claim 3 wherein the centrally-acting analgesic is butorphanol.

* * * * *